(12) United States Patent
Eisenstadt et al.

(10) Patent No.: US 7,629,461 B2
(45) Date of Patent: Dec. 8, 2009

(54) ISOLATED VALACYCLOVIR IMPURITY, PROCESS FOR THE PREPARATION OF VALACYCLOVIR IMPURITY AND USE AS A REFERENCE STANDARD

(75) Inventors: Amihai Eisenstadt, Ramat-Hasharon (IL); Michael Pesachovich, Givat-Shmuel (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 285 days.

(21) Appl. No.: 11/221,124

(22) Filed: Sep. 6, 2005

(65) Prior Publication Data
US 2006/0084668 A1 Apr. 20, 2006

Related U.S. Application Data

(60) Provisional application No. 60/607,279, filed on Sep. 4, 2004.

(51) Int. Cl.
*C07D 473/18* (2006.01)
*G01N 33/15* (2006.01)
(52) U.S. Cl. .................................. 544/276; 436/98
(58) Field of Classification Search ............... 544/276
See application file for complete search history.

(56) References Cited

U.S. PATENT DOCUMENTS

| 4,957,924 | A | * | 9/1990 | Beauchamp | ........... 514/263.38 |
| 6,333,198 | B1 | | 12/2001 | Edmeades et al. | |
| 2003/0153757 | A1 | | 8/2003 | Etinger et al. | |
| 2005/0059684 | A1 | | 3/2005 | Dolitzky et al. | |
| 2005/0070711 | A1 | * | 3/2005 | Lifshitz et al. | ............... 544/276 |
| 2005/0143400 | A1 | * | 6/2005 | Shamai et al. | .......... 514/263.38 |
| 2007/0112193 | A1 | * | 5/2007 | Khunt et al. | ................ 544/276 |

FOREIGN PATENT DOCUMENTS

| WO | WO 97/27197 A | 7/1997 |
| WO | WO 98/03553 A | 1/1998 |
| WO | WO 03/041647 A | 5/2003 |

OTHER PUBLICATIONS

Goodman and Gilman's, *The Pharmacological Basis of Therapeutics* 1193-1198 (9th ed. 1996).
Strobel pp. 391-393, 894, 921, 922, 924, 925 and p. 953, Strobel, H.A.; Heineman, W.R., Chemical Instrumentation: A Systematic Approach, 3rd dd. (Wiley & Sons: New York 1989).
Snyder pp. 549, 552, 571 and 572, Snyder, L.R.; Kirkland, J.J. Introduction to Modern Liquid Chromatography, 2nd ed. (John Wiley & Sons: New York 1979).
Beauchamp et al., "Amino acid ester prodrugs of acyclovir", Antiviral Chemistry & Chemotherapy 3(30): 157-164(1992).

* cited by examiner

*Primary Examiner*—Mark L Berch
(74) *Attorney, Agent, or Firm*—Kenyon & Kenyon LLP

(57) ABSTRACT

The present invention provides an isolated N-formyl valacyclovir, its preparation and its use as a reference marker and/or reference standard.

17 Claims, 3 Drawing Sheets

ISOLATED VALACYCLOVIR IMPURITY, PROCESS FOR THE PREPARATION OF VALACYCLOVIR IMPURITY AND USE AS A REFERENCE STANDARD

CROSS-REFERENCE TO RELATED APPLICATIONS

This application claims the benefit of provisional application Ser. No. 60/607,279, filed Sep. 4, 2004, which is incorporated herein by reference.

FIELD OF THE INVENTION

The present invention relates to an isolated impurity of valacyclovir; N-formyl valacyclovir, its preparation and its use as a reference standard.

BACKGROUND OF THE INVENTION

Valacyclovir is an L-valyl ester prodrug of acyclovir. Acyclovir is an acyclic analog of a natural nucleoside which has been found to have high anti-viral activity. Acyclovir is widely used in the treatment and prophylaxis of viral infections in humans, particularly infections caused by the herpes group of viruses. See Goodman and Gilman's, *The Pharmacological Basis of Therapeutics* 1193-1198 (9th ed. 1996).

Valacyclovir has the chemical name 1-valine, 2-[(2-amino-1,6-dihydro-6-oxo-9H-purin-9-yl)methoxy]ethyl ester. (CAS Registry No. 124832-26-4.) Valacyclovir is currently marketed as VALTREX®. The chemical structure of valacyclovir is shown as Structure I.

Structure I

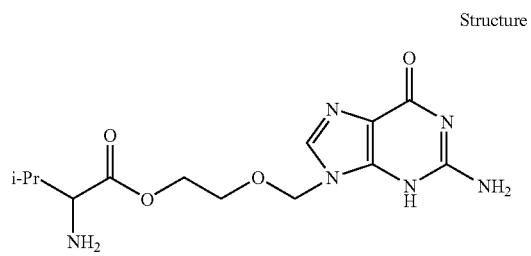

It is well known in the art that, for human administration, safety considerations require the establishment, by national and international regulatory authorities, of very low limits for identified, but toxicologically uncharacterized impurities, before an active pharmaceutical ingredient (API) product is commercialized. Typically, these limits are less than about 0.15 percent by weight of each impurity. Limits for unidentified and/or uncharacterized impurities are obviously lower, typically, less than 0.1 percent by weight. Therefore, in the manufacture of APIs, the purity of the products, such as valacyclovir, is required before commercialization, as is the purity of the active agent in the manufacture of formulated pharmaceuticals.

It is also known in the art that impurities in an API may arise from degradation of the API itself, which is related to the stability of the pure API during storage, and the manufacturing process, including the chemical synthesis. Process impurities include unreacted starting materials, chemical derivatives of impurities contained in starting materials, synthetic by-products, and degradation products.

In addition to stability, which is a factor in the shelf life of the API, the purity of the API produced in the commercial manufacturing process is clearly a necessary condition for commercialization. Impurities introduced during commercial manufacturing processes must be limited to very small amounts, and are preferably substantially absent. For example, the ICH Q7A guidance for API manufacturers requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process.

The product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during processing of an API, such as Valacyclovir, it must be analyzed for purity, typically, by HPLC or TLC analysis, to determine if it is suitable for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and, thus, is as safe as possible for clinical use. As discussed above, in the United States, the Food and Drug Administration guidelines recommend that the amounts of some impurities be limited to less than 0.1 percent.

Generally, side products, by-products, and adjunct reagents (collectively "impurities") are identified spectroscopically and/or with another physical method, and then associated with a peak position, such as that in a chromatogram, or a spot on a TLC plate. (Strobel p. 953, Strobel, H. A.; Heineman, W. R., Chemical Instrumentation: A Systematic Approach, 3rd dd. (Wiley & Sons: New York 1989)). Thereafter, the impurity can be identified, e.g., by its relative position in the chromatogram, where the position in a chromatogram is conventionally measured in minutes between injection of the sample on the column and elution of the particular component through the detector. The relative position in the chromatogram is known as the "retention time."

The retention time can vary about a mean value based upon the condition of the instrumentation, as well as many other factors. To mitigate the effects such variations have upon accurate identification of an impurity, practitioners use the "relative retention time" ("RRT") to identify impurities. (Strobel p. 922). The RRT of an impurity is its retention time divided by the retention time of a reference marker. It may be advantageous to select a compound other than the API that is added to, or present in, the mixture in an amount sufficiently large to be detectable and sufficiently low as not to saturate the column, and to use that compound as the reference marker for determination of the RRT.

Those skilled in the art of drug manufacturing research and development understand that a compound in a relatively pure state can be used as a "reference standard." A reference standard is similar to a reference marker, which is used for qualitative analysis only, but is used to quantify the amount of the compound of the reference standard in an unknown mixture, as well. A reference standard is an "external standard," when a solution of a known concentration of the reference standard and an unknown mixture are analyzed using the same technique. (Strobel p. 924, Snyder p. 549, Snyder, L. R.; Kirkland, J. J. Introduction to Modern Liquid Chromatography, 2nd ed. (John Wiley & Sons: New York 1979)). The amount of the compound in the mixture can be determined by comparing the magnitude of the detector response. See also U.S. Pat. No. 6,333,198, incorporated herein by reference.

The reference standard can also be used to quantify the amount of another compound in the mixture if a "response factor," which compensates for differences in the sensitivity of the detector to the two compounds, has been predetermined. (Strobel p. 894). For this purpose, the reference standard is added directly to the mixture, and is known as an "internal standard." (Strobel p. 925, Snyder p. 552).

The reference standard can serve as an internal standard when, without the deliberate addition of the reference standard, an unknown mixture contains a detectable amount of the reference standard compound using the technique known as "standard addition."

In a the "standard addition technique", at least two samples are prepared by adding known and differing amounts of the internal standard. (Strobel pp. 391-393, Snyder pp. 571, 572). The proportion of the detector response due to the reference standard present in the mixture without the addition can be determined by plotting the detector response against the amount of the reference standard added to each of the samples, and extrapolating the plot to zero concentration of the reference standard. (See, e.g., Strobel, FIG. 11.4 p. 392).

As is known by those skilled in the art, the management of process impurities is greatly enhanced by understanding their chemical structures and synthetic pathways, and by identifying the parameters that influence the amount of impurities in the final product.

Like any synthetic compound, valacyclovir can contain extraneous compounds or impurities that can come from many sources. They can be unreacted starting materials, by-products of the reaction, products of side reactions, or degradation products.

In this application the reference marker is the impurity N-formyl valacyclovir in the API. Detection or quantification of the reference marker serves to establish the level of purity of the API. Use of a compound as a reference marker requires recourse to a sample of substantially pure compound.

SUMMARY OF THE INVENTION

In one aspect, the present invention relates to an isolated N-formyl valacyclovir.

In a further aspect, the present invention relates to a method of making N-formyl valacyclovir including the steps of reacting valacyclovir and ammonium formate to obtain a reaction mixture, combining the reaction mixture with hot water, heating the combination of reaction mixture and hot water, and cooling the combination to obtain a precipitate of N-formyl valacyclovir.

In a further aspect, the present invention relates to the use of N-formyl valacyclovir as a reference marker in a qualitative analysis of valacyclovir.

In another embodiment, the invention is directed to a method of using N-formyl valacyclovir as reference standard to analytically quantify the purity of valacyclovir.

In yet a further aspect, the invention is directed to a method for the quantification of the purity of valacyclovir, comprising the use of N-formyl valacyclovir as reference standard, where the reference standard may be either external standard or internal standard.

DETAILED DESCRIPTION OF THE INVENTION

Figure 1:
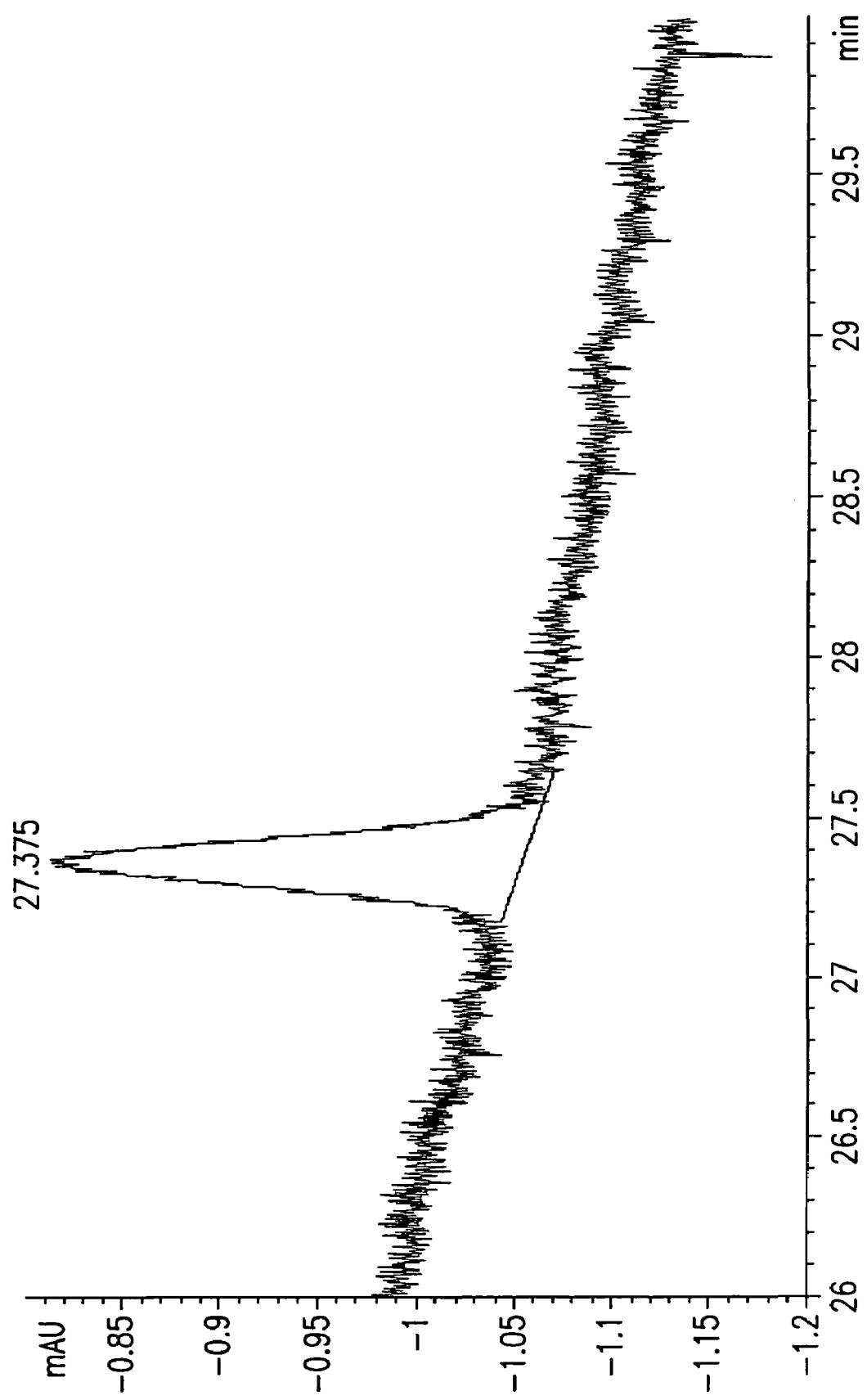
FIG. 1 is a representative HPLC chromatogram from an analysis of a standard solution of N-formyl valacyclovir.

As used herein, the term "isolated" refers to a compound that is at least 90 area-%, as judged by HPLC.

A "reference marker" is used in qualitative analysis to identify components of a mixture based upon their position, e.g., in a chromatogram or on a Thin Layer Chromatography (TLC) plate (Strobel pp. 921, 922, 953). For this purpose, the compound does not necessarily have to be added to the mixture if it is present in the mixture. A "reference marker" is used only for qualitative analysis, while a reference standard may be used for quantitative or qualitative analysis, or both. Hence, a reference marker is a subset of a reference standard, and is included within the definition of a reference standard.

As used herein, the term "reference standard" refers to a compound that may be used both for quantitative and qualitative analysis of an active pharmaceutical ingredient. For example, the HPLC retention time of the compound allows a relative retention time to be determined, thus making qualitative analysis possible. The concentration of the compound in solution before injection into an HPLC (or GC) column allows the areas under the HPLC (or GC) peaks to be compared, thus making quantitative analysis possible.

Reference standards are described in general terms above. However, as will be understood by those skilled in the art, a detector response can be, for example, the peak heights or integrated peak areas of a chromatogram obtained, e.g., by UV or refractive index detection, from the eluent of an HPLC system or, e.g., flame ionization detection (FID) or thermal conductivity detection, from the eluent of a gas chromatograph, or other detector response, e.g., the UV absorbance of spots on a fluorescent TLC plate. The position of the reference standard may be used to calculate the relative retention time for valacyclovir and impurities of valacyclovir.

In one embodiment the present invention provides N-formyl valacyclovir, an impurity of valacyclovir that is isolated from valacyclovir and, in preferred embodiments, substantially free of valacyclovir. In another embodiment, the present invention provides a method for the preparation of N-formyl valacyclovir. In a further embodiment, the present invention relates to the use of N-formyl valacyclovir as a reference marker in a qualitative analysis of valacyclovir. In another embodiment, the invention is directed to a method of using N-formyl valacyclovir as reference standard to analytically quantify the purity of valacyclovir. In yet a further aspect, the invention is directed to a method for the quantification of the purity of valacyclovir, comprising the use of N-formyl valacyclovir as reference standard, where the reference standard may be either external standard or internal standard.

N-formyl valacyclovir, although mentioned in the NDA for valacyclovir (Valtrex®), has never been obtained in substantially pure form, isolated from (that is separate and apart from) valacyclovir. To the best of Applicants' knowledge, the structure of N-formyl valacyclovir has never been discovered before (the location of N-formyl group being unknown).

N-formyl valacyclovir can form during the synthesis of valacyclovir or upon storage, especially if the valacyclovir contains residual process solvents.

The present invention provides an isolated valacyclovir impurity, N-formyl valacyclovir, having the structure (II). To the best of Applicants' knowledge, the structure of N-formyl valacyclovir has never been reported and the compound has never been possessed separate and apart from valacyclovir.

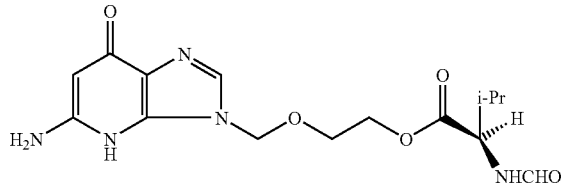

Preferably, the isolated N-formylvalacyclovir comprises from about 0.03 area-% to 5 area-% valacyclovir as judged by HPLC.

More preferably, the isolated N-formyl valacyclovir comprises about 0.03 area-% to about 2 area-% valacyclovir or the isolated N-formyl valacyclovir is at least 95 area-% pure as judged by HPLC.

In a further embodiment, the present invention provides a method of making isolated N-formyl valacyclovir comprising the steps of: reacting valacyclovir with ammonium formate, heating the reaction mixture, combining the resulting hot reaction mixture with hot water, further heating the reaction mixture, cooling the reaction mixture and recovering the N-formyl valacyclovir. Optionally, a solvent is added to the reaction mixture. Preferably, the reaction mixture is obtained in the absence of a solvent. Preferably, the reaction time is of about 1 to about 10 hours. More preferably, the reaction time is of about 2 to about 4 hours. Preferably, the reaction mixture of valacyclovir with ammonium formate is heated to a temperature of about 125° C. to about 145° C. Preferably, the hot water are at a temperature of about 100° C. Preferably, the resulting combination of the reaction mixture with hot water is filtered while hot. Preferably, the reaction mixture is cooled to room temperature. The N-formyl valacyclovir can be recovered (isolated) by any means known in the art, for example filtration (gravity or suction) or centrifugation, to mention just two.

Preferably, N-formyl valacyclovir is recrystallized. More preferably N-formyl valacyclovir is recrystallized from water, to obtain isolated N-formyl valacyclovir.

Manufacturing lot release criteria can be established with reference to a particular amount or concentration of a reference standard in the bulk product. Detection and quantification of the reference standard in the API of a pharmaceutical dosage form can serve as a measure of the shelf-life of the pharmaceutical dosage form. That is, detection of the reference standard at some concentration signals that the API has begun to deteriorate and that efficacy of the API may be compromised. As used herein, HPLC refers to the well-known technique of high-performance liquid chromatography, also referred to as high pressure liquid chromatography. HPLC can be applied to detection and quantification of components of a mixture, for example detection and quantification of impurities in a principal compound such as an active pharmaceutical ingredient (API).

Detection and especially quantification of components of a mixture can be accomplished with the use of response factors. The response of a detector in HPLC (e.g. UV detectors or refractive index detectors) can be and typically is different for each compound eluting from the HPLC column. Response factors, as known, account for this difference in the response signal of the detector to different compounds eluting from the column.

The present invention provides various methods involving the use of N-formyl valacyclovir as reference marker or reference standard.

Provided is a method of identifying N-formyl valacyclovir in a sample of valacyclovir comprising:
(a) providing a reference sample comprising a reference marker and valacyclovir;
(b) carrying out HPLC or TLC on the reference sample to determine the relative retention time of the reference marker compared to valacyclovir;
(c) carrying out HPLC or TLC on the sample of valacyclovir to determine the relative retention time of the N-formyl valacyclovir compared to valacyclovir;
(d) comparing the relative retention times determined in steps (b) and (c);

where, if the relative retention times determined in steps (b) and (c) are substantially the same, the N-formyl valacyclovir is identified as being the same as the reference marker.

Also provided is a method of determining the amount of an impurity in a sample of valacyclovir comprising:
(a) adding a known amount of a reference standard to the valacyclovir sample;
(b) subjecting the valacyclovir to HPLC;
(c) identifying and measuring the area of an HPLC peak associated with the N-formyl valacyclovir;
(d) identifying and measuring the area of an HPLC peak associated with the reference standard;
(e) calculating the amount of the impurity in the valacyclovir sample based on the results of steps (c) and (d);
where the reference standard is N-formyl valacyclovir.

Also provided is a method of determining the amount of N-formyl valacyclovir in a sample of valacyclovir comprising:
(a) providing a sample of valacyclovir containing an unknown concentration of the N-formyl valacyclovir;
(b) providing a sample of a known concentration of the N-formyl valacyclovir;
(c) subjecting a portion of the sample of valacyclovir and a portion of the sample of the N-formyl valacyclovir to HPLC;
(d) measuring the area of the N-formyl valacyclovir peaks obtained from the sample of valacyclovir and from the sample of the N-formyl valacyclovir; and
(e) calculating the concentration of the N-formyl valacyclovir in the sample of valacyclovir from the measurements of step (d).

Also provided is a method of determining the amount of N-formyl valacyclovir in a sample of valacyclovir comprising:
(a) providing a first reference solution of known concentration of substantially pure valacyclovir,
(b) providing a second reference solution of known concentration of substantially pure N-formyl valacyclovir of known concentration;
(c) subjecting an aliquot of each of the first and second reference solutions to HPLC analysis and determining the response factors of valacyclovir and N-formyl valacyclovir;
(d) providing a solution of known overall concentration of the valacyclovir;
(e) subjecting the solution to HPLC analysis under substantially the same conditions used in step (c); and
(f) calculating the amount of N-formyl valacyclovir in the solution using the respective peak areas and the response factors.

The response factor is calculate as follows: If Y is the primary or principal component, the relative response factor of compound X, i.e. an impurity in Y and especially a reference marker for the purity of Y, can be expressed as:

$$R_{Y/X} = [M_X M_Y]/[A_X/A_Y]$$

where $M_X$ and $M_Y$ are the known molar amounts or concentrations of X and Y in a standard solution (a solution having known amount of X and Y) and $A_X$ and $A_Y$ are the detector responses, for example peak areas in HPLC, for species X and Y, respectively.

Then, in a solution having a known total amount of sample but unknown relative amounts of Y and X:

$$M'_X/M'_Y = R_{Y/X} * [A'_X/A'_Y]$$

where $M'_X$ and $M'_Y$ are the amounts of X and Y, respectively, in the solution and $A'_X$ and $A'_Y$ are the associated detector responses for X and Y.

Determination of response factors requires access to samples of substantially pure X and Y, especially when X is a reference marker for the purity of Y. The present invention provides N-formyl valacyclovir in isolated form, suitable for use as a reference standard.

Determination of the purity of valacyclovir in a pharmaceutical dosage form that includes valacyclovir, for example to evaluate shelf life and residual potency, requires that the valacyclovir be separated from excipients and other intentionally added ingredients in the dosage form. This can be accomplished by, for example, combining a suitable quantity of the dosage form, comminuted if desired, with a suitable solvent. Suitable solvents dissolve valacyclovir and impurities therein, especially N-formyl valacyclovir, but do not dissolve excipients and other intentionally added ingredients The present invention provides a process for preparing a pharmaceutical composition comprising valacyclovir or a pharmaceutically acceptable salt thereof which comprises formulating valacyclovir or a pharmaceutically acceptable salt, tested according to any of the methods, which are part of this invention, above with an excipient of carrier.

Detection and especially quantification of components of a mixture by HPLC requires that the peaks for the components be sufficiently separated (resolved). This can be checked by performing a system suitability check to determine the resolution factors according to a method such as described below.

The well-known technique of thin layer chromatography (TLC) can also be applied to assessment of the purity of an API. In this case, presence of an impurity, e.g. a reference marker, is established by the presence of a suitably-visualized "spot" at the same, simultaneously determined relative position, $R_F$, (relative to the solvent front) of the reference marker.

In yet another embodiment, the present invention provides a method of testing or proofing the purity of valacyclovir, either in bulk or isolated from a pharmaceutical dosage form that includes valacyclovir. The method includes the step of testing the valacyclovir by HPLC or TLC to determine the presence of N-formyl valacyclovir in the valacyclovir. The herein below described HPLC method is an example of an analytical technique suitable for this testing or proofing.

EXAMPLES

Example 1

Quantitative Analysis of N-Formyl Valacyclovir in Valacyclovir

A. Chromatographic Method

Quantitative analysis of valacyclovir may be performed using the following achiral HPLC method:

The chromatographic method utilizes a suitable chromatography column such as the reverse phase column C18 and gradient HPLC mode.

| Column & Packing: | Inertsil ODS-3V 5µ 250 × 4.6 mm | | |
|---|---|---|---|
| Eluent A: | 98% 0.01M Potassium Dihydrogen Phosphate in water adjusted to pH-3.5 with 10% $H_3PO_4$ and 2% Acetonitrile | | |
| Eluent B: | acetonitrile | | |
| Gradient: | Time (min) | % A | % B |
|  | 0 | 100 | 0 |
|  | 5 | 100 | 0 |
|  | 32 | 87 | 13 |
| Equilibration time: | 7 min | | |
| Flow Rate: | 1.5 mL/min | | |
| Detector: | 254 nm (UV) | | |
| Sample Volume: | 20 µL | | |
| Diluent: | Eluent A | | |

B. Standard Solution Preparation of N-Formyl-Valcyclovir for Identification of N-Formyl-Valcyclovir:

A solution of N-formyl-valcyclovir standard in diluent was prepared. The peak of N-formyl-valcyclovir was identified at RT=27.4 minutes. A chromatogram of the standard is shown in FIG. 1.

Figure 2:
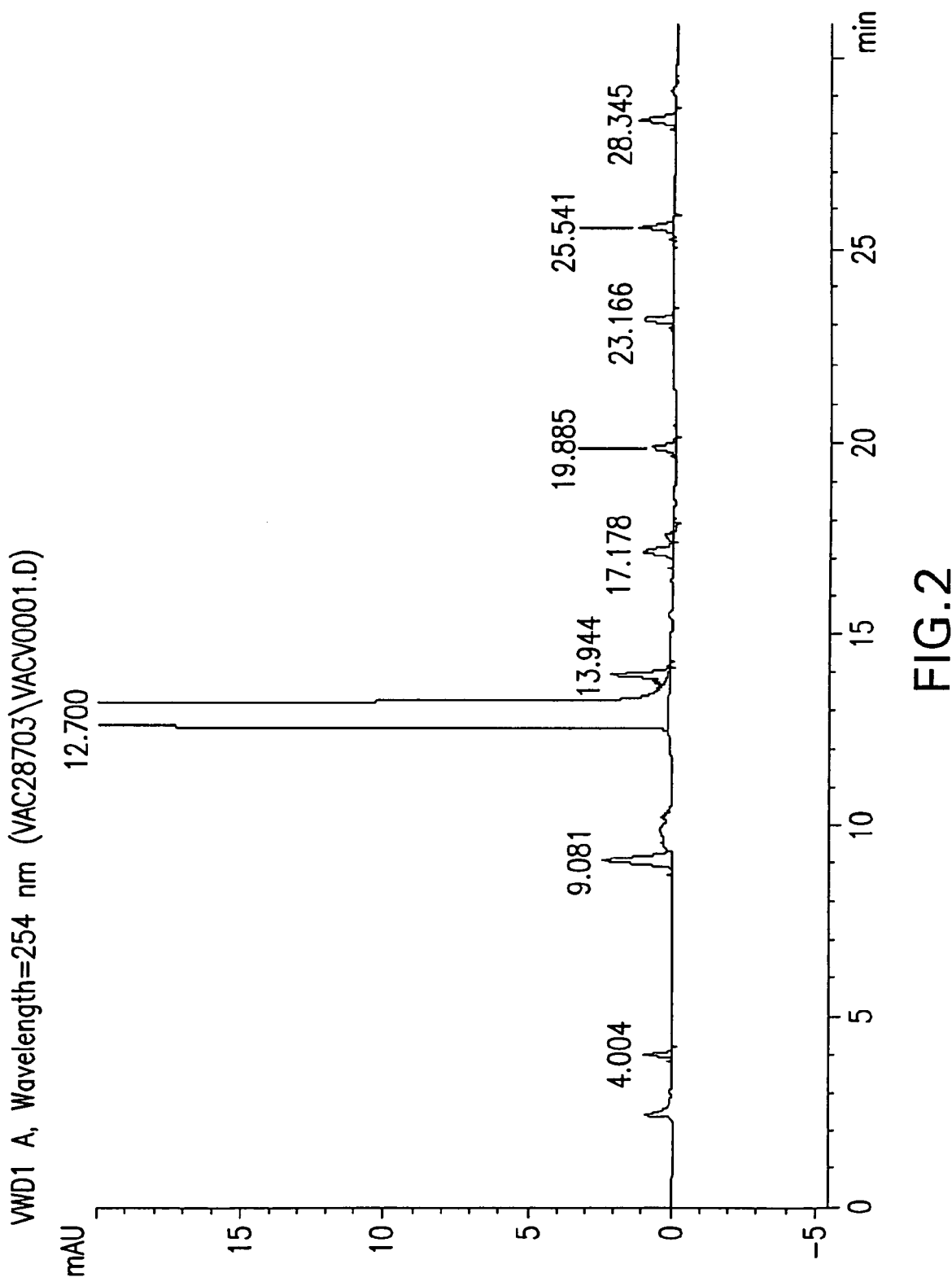
FIG. 2 is a representative HPLC chromatogram of a marker solution of N-formyl valacyclovir.

C. Marker Solution Preparation for Identification of N-Formyl-Valcyclovir:

Marker Solution of valacyclovir containing N-formyl-valcyclovir in a concentration of about 0.8 mg/mL of a diluent was prepared. The marker solution containing N-formyl-valcyclovir was injected in order to identify peak of N-formyl-valcyclovir impurity in Valcyclovir sample. The peak of N-formyl-valcyclovir was identified (according to the peak obtained in the Standard Solution) at RT=28.345 minutes. A typical chromatogram of marker containing N-formyl-valacyclovir is shown in FIG. 2.

D. Sample Solution Preparation:

A solution of valacyclovir for analysis with a concentration of about 0.8 mg/ of a diluent was prepared.

E. Procedure:

Marker and sample solutions were injected into chromatograph continuing the chromatogram of samples up to the end of gradient program.

Figure 3:
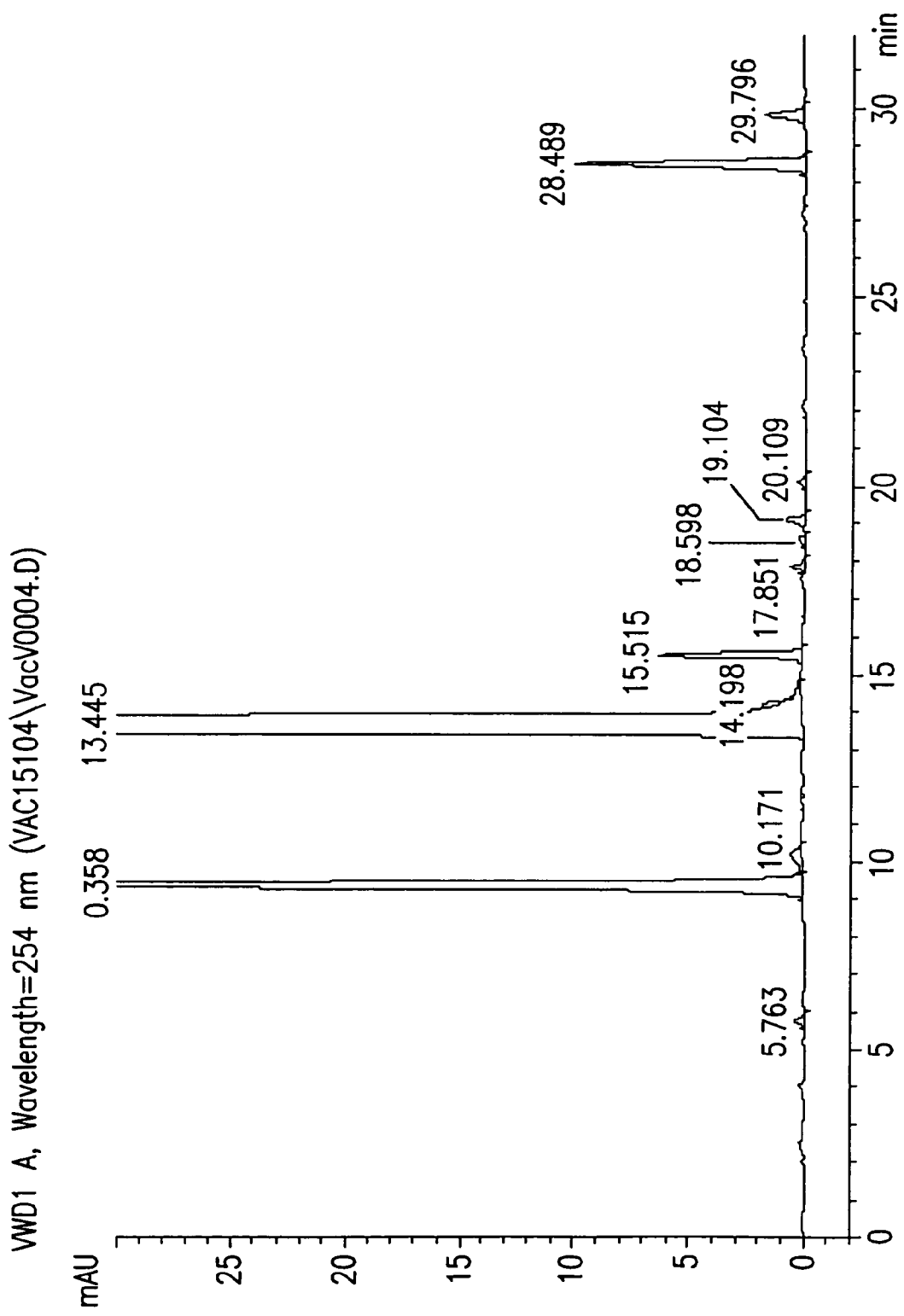
FIG. 3 is a representative HPLC chromatogram of valacyclovir sample containing N-formyl valacyclovir.

The sample chromatogram is shown in FIG. 3.

The peaks areas are determined using a suitable integrator as known in the art.

Calculations:

$$\% \text{ impurity } i = \frac{\text{Area impurity } i * RRF}{\sum \text{all areas + area of impurity} * RRF_{\text{Valacyclovir}}} \times 100$$

$RRF$—relative response factor of impurity/RRF Valacyclovir

The DL is about 0.01%; the QL is about 0.03%

Example 2

Preparation of N-Formyl Valacyclovir

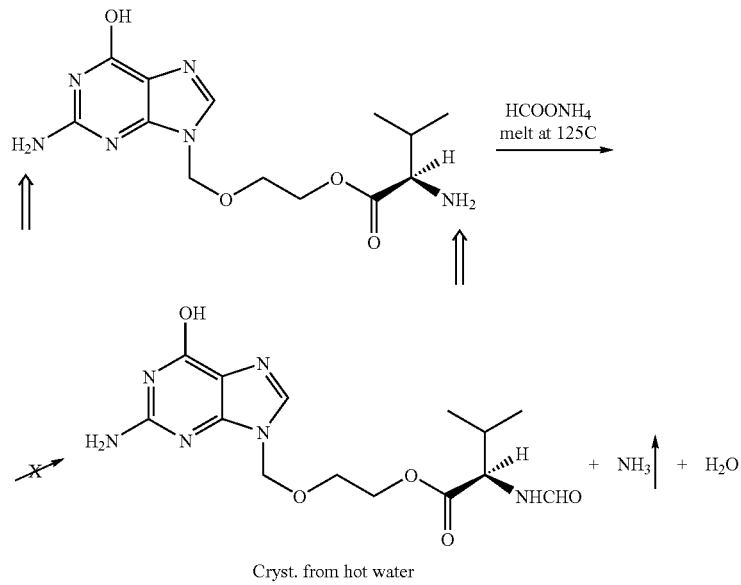

A 150-ml one necked round-bottomed flask were equipped with magnetic stirring bar and closed with $CaCl_2$ tube was charged with 10.8 g (0.03M) g valacyclovir, and 2.1 g (0.033M) ammonium formate. The heterogeneous reaction mixture was heated in an oil bath thermostatted at 125° C. for 2.5 hrs with vigorous stirring of the contents of the flask. The solid mixture melted with the release of ammonia gas and water vapors.

The reaction mixture was transferred while hot with 30 ml boiling water into the crystallization flask to which 250 ml hot water were added. The mixture was heated until it turns clear. Any insoluble impurities were removed by quick, hot filtration through a glass wool plug. The filtrate was allowed to stand for 8 hrs at room temperature to give, after filtration, white powder, 9.5 g with a purity of 85.39%.

The same crystallization procedure was repeated twice, from hot water (150 ml and 75 ml respectively), and yielded 4.5 g with a purity of 95.85 area-%.

The $^1H$ and $^{13}C$-NMR together with the 2D experiments data indicate that the CHO group is attached to the valine-$NH_2$ moiety in the valacylovir molecule.

Example 3

Preparation of N-Formyl Valacyclovir

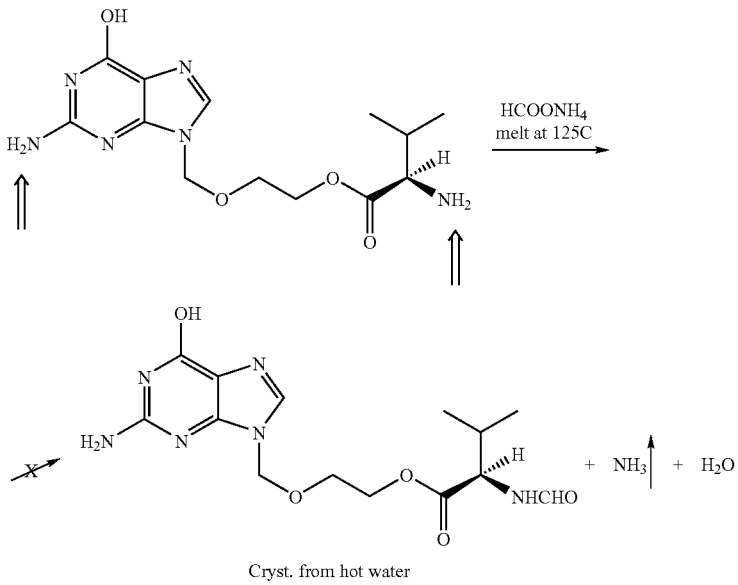

A 150-ml one necked round-bottomed flask were equipped with magnetic stirring bar and closed with $CaCl_2$ tube was charged with 10.8 g (0.03M) g valacyclovir, and 2.1 g (0.033M) ammonium formate. The heterogeneous reaction mixture was heated in an oil bath thermostatted at 145° C. for 2.5 hrs with vigorous stirring of the contents of the flask. The solid mixture melted with the release of ammonia gas and water vapors.

The reaction mixture was transferred while hot with 30 ml boiling water into the crystallization flask to which 250 ml hot water were added. The mixture was heated until it turns clear. Any insoluble impurities were removed by quick, hot filtration through a glass wool plug. The filtrate was allowed to stand for 8 hrs at room temperature to give, after filtration, white powder, 10.4 g with a purity of 80%.

The same crystallization procedure was repeated, from hot 150 ml water, and yielded 9.0 g with a purity of 92.4 area-%.

Example 4

Preparation of N-Formyl Valacyclovir

A 100 ml round bottom flask equipped with magnetic stir bar is charged with 7.25 gr Valacyclovir (20 mmol), 1.97 gr ammonium formate (31.2 mmol), NMP (N-Methyl-pyrrolidone) (15 ml) is added and stirring is started. The resulting mixture is placed in an oil bath that is heated to 125° C. for 2 hrs. The mixture is removed from the oil bath, allowed to cool to room temperature, and the solvent is removed under reduced pressure using high vac. pump. The residue is crystallized from 150 ml boiling water to give 6.0 gr at the purity of 80%.

The invention claimed is:

1. Isolated N-formylvalacyclovir.
2. The isolated N-formylvalacyclovir of claim 1, comprising from about 0.03 area-% to 5 area-% valacyclovir by HPLC.
3. The isolated N-formyl valacyclovir of claim 2, comprising about 0.03 area-% to about 2 area-% valacyclovir by HPLC.
4. The isolated N-formyl valacyclovir of claim 1, which is at least 95 area-% pure by HPLC.
5. A method of preparing N-formylvalacyclovir comprising:
   a) combining valacyclovir with ammonium formate to form a reaction mixture;
   b) heating the reaction mixture;
   c) combining the reaction mixture from step a) with hot water;
   d) heating the reaction mixture;
   e) cooling the heated reaction mixture; and
   f) recovering the N-formyl valacyclovir from the cooled reaction mixture.
6. The method of claim 5, wherein a solvent is added in step a).
7. The method of claim 5 further comprising the step of isolating the N-formyl valacyclovir.
8. The method of claim 5 wherein the reaction time is about 1 to about 10 hours.
9. The method of claim 8 wherein the reaction time is about 2 to about 4 hours.
10. The method of claim 5 wherein the reaction mixture of valacyclovir and ammonium formate is heated to about 125° C. to about 145° C.
11. The method of claim 5 wherein the hot water in step c) is at a temperature of about 100° C.
12. The method of claim 5 wherein the reaction mixture in step d) is filtered while hot.
13. The method of claim 5 wherein the reaction mixture in step e) is cooled to room temperature.
14. The method of claim 5 wherein the N-formyl valacyclovir is recrystallized.
15. The method of claim 14 wherein the N-formyl valacyclovir is recrystallized from water.
16. A method of determining the amount of N-formyl valacyclovir in a sample of valacyclovir comprising:
   (a) adding a known amount of N-formyl valacyclovir to the valacyclovir sample;
   (b) subjecting the valacyclovir to HPLC;
   (c) identifying and measuring the area of an HPLC peak associated with the N-formyl valacyclovir;
   (d) identifying and measuring the area of an HPLC peak associated with the reference standard; and
   (e) calculating the amount of the N-formyl valacyclovir in the valacyclovir sample based on the results of steps (c) and (d).
17. A method of determining the amount of N-formyl valacyclovir present as an impurity in a sample of valacyclovir comprising:
   a) providing a sample of valacyclovir containing an unknown concentration of the impurity, N-formyl valacyclovir;
   b) providing a sample of N-formyl valacyclovir that has a known concentration;
   c) subjecting a portion of the sample of valacyclovir of step (a) and a portion of the sample of N-formyl valacyclovir of step (b) to HPLC;
   d) measuring the area of N-formyl valacyclovir peaks obtained from the sample of valacyclovir and from the sample of the known concentration of N-formyl valacyclovir; and
   e) calculating the concentration of N-formyl valacyclovir in the sample of valacyclovir from the measurements of step (d).

* * * * *